United States Patent
Imran (10) Patent No.: US 9,893,654 B2
(45) Date of Patent: *Feb. 13, 2018

(54) ENERGY HARVESTING MECHANISM (71) Applicant: Incube Labs, LLC, San Jose, CA (US)

(72) Inventor: Mir A. Imran, Los Altos Hills, CA (US)

(73) Assignee: InCube Labs, LLC, San Jose, CA (US)

( * ) Notice: Subject to any disclaimer, the term of this patent is extended or adjusted under 35 U.S.C. 154(b) by 339 days.

This patent is subject to a terminal disclaimer.

(21) Appl. No.: 14/569,046

(22) Filed: Dec. 12, 2014

(65) Prior Publication Data

US 2015/0137665 A1 May 21, 2015

Related U.S. Application Data

(62) Division of application No. 12/556,524, filed on Sep. 9, 2009, now Pat. No. 8,948,870.

(Continued)

(51) Int. Cl.
*H02N 2/18* (2006.01)
*A61N 1/378* (2006.01)
*H01L 41/113* (2006.01)

(52) U.S. Cl.
CPC .......... *H02N 2/186* (2013.01); *A61N 1/3785* (2013.01); *H01L 41/113* (2013.01)

(58) Field of Classification Search
CPC ..... A61N 1/3785; A61N 1/378; A61N 1/3718

(Continued)

(56) References Cited

U.S. PATENT DOCUMENTS 3,456,134 A 7/1969 Wen
3,563,245 A 2/1971 McLean et al.
(Continued)

FOREIGN PATENT DOCUMENTS

JP 2004-115655 2/2004
JP 2007-281015 10/2007
(Continued)

OTHER PUBLICATIONS

First examination Report dated Oct. 3, 2013 in Australian Application 2009298928.

(Continued)

*Primary Examiner* — Michael Carey
*Assistant Examiner* — Roland Dinga
(74) *Attorney, Agent, or Firm* — Mahamedi IP Law LLP; Joel Harris (57) ABSTRACT

Embodiments of the invention provide an energy harvesting mechanism comprising a central conductive element and a plurality of transductive elements. Each transductive element is positioned to be in contact with a corresponding peripheral length segment of the central conductive element. Also each transductive element is deformable in a characteristic radial direction to convert its deformation into a corresponding electrical signal. The plurality of transductive elements are arranged so that any one of the plurality of transductive elements is capable of being deformed in the characteristic radial direction to trigger the corresponding electrical signal. Embodiments of the mechanism can be used for harvesting energy from a variety of bio-kinetic events such as a heartbeat, respiration, muscle contraction or other movement. Such embodiments can be used for powering a variety of implanted medical devices such as pacemakers, defibrillators and various monitoring devices.

20 Claims, 6 Drawing Sheets

Related U.S. Application Data (60) Provisional application No. 61/095,619, filed on Sep. 9, 2008.

(58) Field of Classification Search
USPC ...... 607/33–35; 310/334–336, 357–358, 367
See application file for complete search history.

(56) References Cited

U.S. PATENT DOCUMENTS

| | | | |
|---|---|---|---|
| 3,693,625 | A | 9/1972 | Auphan |
| 4,613,784 | A | 9/1986 | Haun et al. |
| 4,690,143 | A | 9/1987 | Schroeppel |
| 4,780,638 | A | 10/1988 | Reinelt et al. |
| 4,798,206 | A | 1/1989 | Maddison et al. |
| 5,431,694 | A | 7/1995 | Snaper et al. |
| 5,615,466 | A | 4/1997 | Safari et al. |
| 5,869,189 | A | 2/1999 | Hagood et al. |
| 6,131,581 | A | 10/2000 | Leysieffer et al. |
| 6,337,835 | B1 | 1/2002 | Sporn et al. |
| 6,822,343 | B2 | 11/2004 | Estevez |
| 6,963,157 | B2 | 11/2005 | Sato et al. |
| 7,084,605 | B2 | 8/2006 | Mickle et al. |
| 7,130,681 | B2 | 10/2006 | Gebhardt et al. |
| 7,292,888 | B2 | 11/2007 | Deno et al. |
| 7,365,455 | B2 | 4/2008 | Hamel et al. |
| 7,629,727 | B2 | 12/2009 | Whinnery |
| 8,311,632 | B2 | 11/2012 | Pless et al. |
| 8,948,870 | B2 * | 2/2015 | Imran ................ A61N 1/3785 607/35 |
| 2002/0011300 | A1 | 1/2002 | Cass |
| 2002/0053801 | A1 | 5/2002 | Herman |
| 2003/0056351 | A1 | 3/2003 | Wilkie et al. |
| 2003/0141785 | A1 | 7/2003 | Sato et al. |
| 2004/0073267 | A1 | 4/2004 | Holzer |
| 2005/0012434 | A1 | 1/2005 | Pizzochero et al. |
| 2005/0110277 | A1 | 5/2005 | Adamson et al. |
| 2005/0274176 | A1 | 12/2005 | Thiesen et al. |
| 2006/0184206 | A1 | 8/2006 | Baker et al. |
| 2007/0078492 | A1 | 4/2007 | Tozzi et al. |
| 2007/0088402 | A1 | 4/2007 | Melvin |
| 2007/0293904 | A1 | 12/2007 | Gelbart et al. |
| 2008/0119421 | A1 | 5/2008 | Tuszynski et al. |
| 2008/0136292 | A1 | 6/2008 | Thiesen |
| 2008/0150396 | A1 | 6/2008 | Clingman |
| 2008/0200963 | A1 | 8/2008 | Pless et al. |
| 2008/0203849 | A1 | 8/2008 | Hagg |
| 2008/0262562 | A1 | 10/2008 | Roberts et al. |
| 2009/0152990 | A1 | 6/2009 | Brown et al. |
| 2009/0167034 | A1 | 7/2009 | Waters et al. |
| 2009/0167110 | A1 | 7/2009 | Berkcan et al. |
| 2009/0171448 | A1 | 7/2009 | Eli |
| 2009/0216292 | A1 | 8/2009 | Pless et al. |
| 2010/0049269 | A1 | 2/2010 | Tran et al. |
| 2010/0063557 | A1 | 3/2010 | Imran |
| 2010/0076517 | A1 | 3/2010 | Imran |
| 2010/0171394 | A1 | 7/2010 | Glenn et al. |

FOREIGN PATENT DOCUMENTS

| | | |
|---|---|---|
| JP | 2008-516739 | 5/2008 |
| JP | 2009-529975 | 8/2009 |
| JP | 4477638 B2 | 6/2010 |
| WO | WO 2006/024868 A2 | 3/2006 |
| WO | WO 2007/068284 | 6/2007 |
| WO | WO 2007/109272 A2 | 9/2007 |
| WO | WO 2007/149462 A2 | 12/2007 |
| WO | WO 2008/085886 A2 | 7/2008 |
| WO | WO 2010/039497 | 4/2010 |

OTHER PUBLICATIONS

Second Examination Report dated Oct. 1, 2013 in European Application 09818246.2.
Second Office Action dated Jul. 23, 2013 in Chinese Application No. 200980142008.9.
First Office Action dated Sep. 24, 2013 in Japanese Application No. 2011-529162.
Nissi, "Fast Heart Rate (more than 100 beats per minute) without obvious cause." Apr. 27, 2007, WebMD: http/www.webmd.com/a-to-z-guieds/fast-heart-rate-more-than-100-beats-per-minute-without-obvious-cause.
First Examination Report dated Jan. 23, 2013 in European Application No. 09818246.2.
International Preliminary Report on Patentability dated Mar. 29, 2011 in International Application No. PCT/US2009/057855.
Office Action dated Aug. 31, 2012 in corresponding Chinese Application 200980142008.9.
International Preliminary Report on Patentability dated Mar. 15, 2011 in International Application No. PCT/US2009/056402.
International Search Report and Written Opinion dated May 3, 2010 in International Application No. PCT/US2009/057855.
International Search Report and Written Opinion dated Feb. 2, 2010 in International Application No. PCT/US2009/056402.
Office Action dated Aug. 11, 2015 in corresponding Japanese Application 2014197996.

* cited by examiner

ENERGY HARVESTING MECHANISM

RELATED APPLICATIONS

This application is a divisional of U.S. patent application Ser. No. 12/556,524 filed Sep. 9, 2009, entitled ENERGY HARVESTING MECHANISM, which claims the benefit of Provisional U.S. Patent Application No. 61/095,619, filed Sep. 9, 2008, entitled ENERGY HARVESTING MECHANISM. The aforementioned applications are hereby incorporated by reference herein in their entirety for all purposes.

BACKGROUND OF THE INVENTION

Field of the Invention

Embodiments described herein relate to energy materials. More particularly embodiments described herein related to harvesting material and mechanism for use in biomedical and other applications.

Various implanted a medical devices such as implanted pacemakers have long term power needs that may be met by energy harvesting mechanisms that "harvest" energy from bio kinetic events or movements, such as from a beating heart. Such mechanisms may be positioned to deform in response to bio-kinetic events or movement of the host, for purpose of generating electrical signals that can be used for a desired purpose. However, conventional approaches for using energy harvesting mechanisms have had some drawbacks. For example, conventional energy harvesting mechanisms are generally deformable to generate electrical current from force applied in only one general direction. As such, conventional energy harvesting mechanisms require consideration in the manner they are oriented when used and can be limited in their application. Thus there is a need for energy harvesting mechanisms that can generate electrical power from deformation in any direction

BRIEF SUMMARY OF THE INVENTION

Various embodiments described herein provide a process and mechanism for enabling energy harvesting in various applications including various biomedical applications. Still further, embodiments described herein enable a process for the use of an energy harvesting material and mechanism that can generate voltage in response to deformation of the material in any direction, as opposed to a limited number of directions. Various applications of embodiments of the energy harvesting materials and mechanisms described herein include medical implants such as pacemakers, monitoring instrumentation as well for use in portable electronic devices such as cell phones and other personal communication devices. However, numerous other applications are contemplated by embodiments of the invention, for example, in harvesting wind energy.

In one embodiment, the invention provides an energy harvesting mechanism comprising, a central conductive element such as a conductive rod and a plurality of transductive element. Each of the transductive elements is positioned to be in contact with a corresponding peripheral length segment of the central conductive element. Also each of the transductive elements is deformable in a characteristic radial direction to convert its deformation into a corresponding electrical signal. The plurality of transductive elements are arranged so that any one of the plurality of transductive elements is capable of being deformed in the characteristic radial direction to trigger the corresponding electrical signal.

Typically, the plurality of transductive elements will comprise piezoelectric (hereafter "PZT") fiber with at least a portion of the fibers including a plurality of peripheral conductive elements, positioned on a periphery of the fiber the conductive element. The peripheral conductive elements can be formed on the fiber using sputter, screen printing or other process known in the art. The central conducive rod includes an insulative layer that is layered on a periphery of the conductive element to partially expose regions of the conductive element. Each PZT fiber is positioned relative to the conductive element so that individual peripheral conductive elements of the PZT fiber align with a corresponding exposed region of the central conductive element.

In some embodiments, each peripheral conductive element of each PZT fiber is aligned in a substantially parallel fashion with spatially corresponding peripheral conductive elements of other PZT fibers in the plurality of PZT fibers to form a group of peripheral conductive elements so that the electrical signal developed from deformation of any of the PZT fibers in the plurality of PZT fibers can be conducted through any of the peripheral conductive elements of the group.

Further details of these and other embodiments of energy harvesting mechanisms, related fabrication processes and various methods of use of the mechanism are described more fully below with reference to the attached figures.

BRIEF DESCRIPTION OF THE DRAWINGS

FIG. 2b is a cross sectional end view of the embodiment of FIG. 2a.

FIG. 4a is a lateral view illustrating an embodiment of a central conductive rod including insulated and conductive regions.

FIG. 4b is a cross sectional end view of the embodiment of FIG. 4a.

FIG. 5b is a cross sectional end view of the embodiment of FIG. 5a.

DETAILED DESCRIPTION OF EMBODIMENTS

Various embodiments described herein provide for an energy harvesting mechanism that comprises a bundle or assembly of individual transductive fibers or elements, combined with a central rod or conductive member. As will be described, embodiments enable a energy harvesting mechanism useful in one or more biomedical applications that can generate electrical signals in response to being deformed in any one of many possible radial directions.

Various implanted medical devices such as implanted pacemakers have long term power needs that may be met by energy harvesting mechanisms that "harvest" energy from bio-kinetic events or movements, such as from a beating heart or respiration. Such mechanisms may be positioned to deform in response to bio-kinetic events or movement of the host, for the purpose of generating electrical signals that can be used for a powering the medical implant or other desired purpose. However, conventional approaches for using energy harvesting mechanisms have had some drawbacks. For example, conventional energy harvesting mechanisms are generally deformable to generate electrical current from force applied in only one general direction. As such, conventional energy harvesting mechanisms require consideration in the manner they are oriented when used and can be limited in their application.

In contrast, embodiments described herein enable an energy harvesting mechanism to generate current from deformation in multiple directions, so as to be responsive to bio-kinetic events or movement from any one of many possible directions. They are also applicable to wind energy harvesting applications where a wind energy collector, such as a sail or a pennant is deformed in multiple directions from blowing wind.

Figure 1:
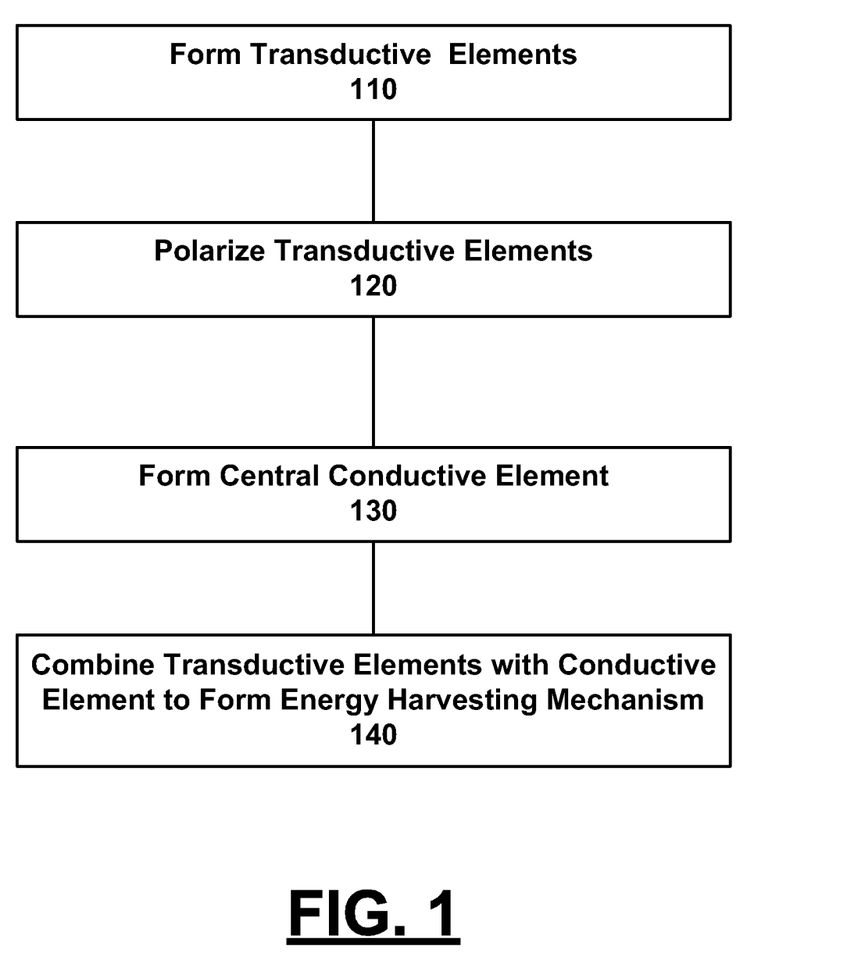
FIG. 1 illustrates an embodiment of a process for forming an energy harvesting mechanism that is responsive to deformation in one or more directions.

FIG. 1 illustrates an embodiment of a process for forming an energy harvesting mechanism that is responsive to deformation in one or more directions (e.g. multiple radial directions). In describing an embodiment of FIG. 1, reference is made to elements of other subsequent figures to illustrate suitable components or elements for implementing a step or sub-step being described.

In step 110, transductive elements are formed for inclusion in a periphery of the energy harvesting assembly also referred to as bundle 500. In an embodiment, the transductive elements may be axial or elongated, such as in the form of fibers or strands.

Figure 2A:
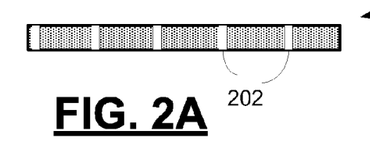
FIG. 2a is a lateral view illustrating an embodiment of a transductive axial element comprising a PZT fiber.
Figure 2B:
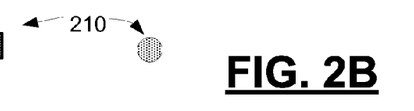

With reference to FIGS. 2A and 2B, transductive axial elements 210 are shown in the form of piezoelectric or PZT fibers 210 that have peripheral conductive elements 202 formed thereon. As is described herein, deformation of PZT fibers 210 results in the generation of a voltage. Peripheral conductive elements 202 serve to conduct that current generated from fibers 210 to either central rod 410, external wires coupled to fibers 210 or to another coupled electrically conductive member of conduit. Accordingly, peripheral conductive elements 202 are also referred to herein as electrodes 202. The diameter of the PZT fibers 210 may range between about 20 μm to about 500 μm and are typically about 100 μm. Suitable materials for PZT fibers 210 include various ceramics including lead-zirconate-titanate (PZT), lead-titanate (PbTiO2), lead-zirconate (PbZrO3), and barium-titanate (BaTiO3). Various crystalline piezoelectric materials may also be used including quartz and berlinite. Use of various pettier materials for transductive elements 202 and fibers 210 is also contemplated.

The peripheral conductive elements 202 may be formed using processes such as sputtering or screen printing, and may be patterned and spaced on the periphery of the respective fiber. Peripheral conductive elements 202 may be formed, for example, from silver, gold, copper, as well as alloys thereof or other suitable conductive metal or conductive material (e.g., conductive polymers). The pattern and spacing of the peripheral conductive elements 202 on the PZT fiber 210 may be selected based on aligning the peripheral conductive elements to make electrical contact with exposed metal regions of a central conductive rod or axial element (as is described below).

FIG. 2B shows an end view of the PZT fiber 210. In an implementation shown, the PZT fiber is cylindrical; however, non-circular cross-sections (e.g., rectangular) may also be used. For optimal geometry, a diameter of the fiber 210 should be less than or equal to a diameter of the conductive rod 410 described below. However, other configurations for the relationship between the diameter of fibers 210 and that of rod 410 are also contemplated.

Figure 3:
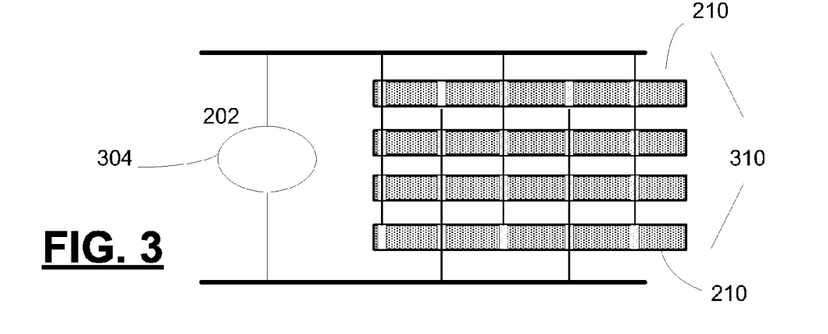
FIG. 3 is a schematic illustrating an embodiment of a circuit for producing PZT fibers.

In step 120 (FIG. 1), the transductive elements (e.g., the PZT fiber 210) are polarized. FIG. 3 shows that the PZT fiber 210 is placed in a fixture 310 where it is subjected to a high polarizing voltage 304 in a process known as polling. The result of performing step 120 is that regions within the structure of the PZT fiber 210 become polarized with positive and negative electrical charges. While the regions of positive and negative charges within the structure of the PZT fiber are separated, they are symmetrically distributed, so that the structure of the PZT fiber overall is electrically neutral. More specifically, the random ferroelectric domains within the structure of the PZT fiber become aligned to an induced electric field from the polarizing voltage resulting in a symmetrical distribution of regions of positive and negative charge. When the fibers, are deformed the charge symmetry is disturbed, and the charge asymmetry generates a voltage across the fibers. The amount of voltage and/or power generated by fibers is a function of the amount of deformation (e.g., strain) and the frequency of deformation. Generally, within certain limitations of the material properties of the PZT fibers, increased amounts of deformation of the fiber and the frequency of deformation will result in increased voltage and increased power generation.

Figures 4A, 4B:
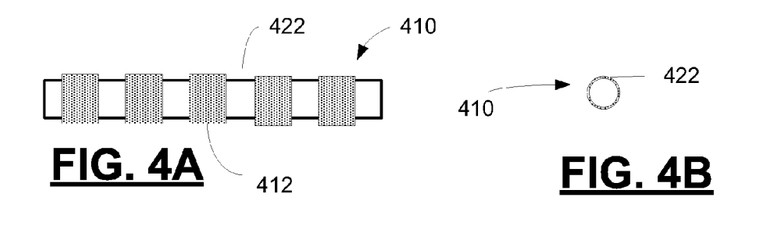

As a separate and independent step, step 130 (FIG. 1) provides for formation of a central conductive element. In an embodiment, the central conductive element may be elongated, such as in the form of a rod. The element can have other shapes including rectangular or spherical. FIG. 4A illustrates a central conductive element 410, according to an embodiment. The central conductive element 410 may correspond to a metal rod. FIG. 4B shows an end view of the rod (circular). In an embodiment, the cross-section of the central rod 410 is dimensioned to be about the same (or greater) as the cross-section of each of the individual PZT fibers 210.

With reference to FIG. 4A, the central rod 410 typically includes an insulative sheath or layer 412 that is patterned or otherwise formed on the periphery of the central rod so as to provide exposed conductive regions 422. Exposed regions 422 can then be aligned or otherwise matched up with conductive portions 202 so that current can flow between regions 422 and conductive portions 202. In other embodiments, described herein conductive portions 202 can also aligned or otherwise be matched up with corresponding conductive portions of one or more wires other conductive members placed in contact with the external surface of fibers 210. In use, such embodiments provide a circuit for the flow of current from fibers 210 via peripheral conductive elements 202 to circuitry of a device to be powered by mechanism 500 and the back to fibers 210 through conductive rod 410.

Figure 5A:
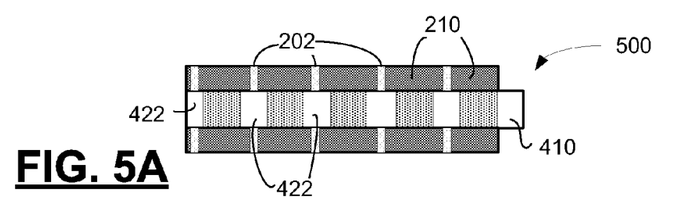
FIG. 5a is a lateral view illustrating an embodiment of the energy harvesting mechanism/fiber bundle including a central conductive rod surrounded by PZT fibers.
Figure 5B:
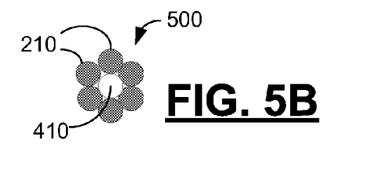

Step 140 provides that the transductive elements (e.g., individual PZT fibers 210) are combined with the central conductive rod 410 to form an energy harvesting mechanism or bundle 500. With reference to an embodiment shown in FIG. 5A, an axial view of the energy harvesting mechanism 500 is shown. FIG. 5B illustrates an end view of the energy harvesting mechanism 500 formed from the central rod 410 and transductive axial elements (PZT fiber 210) so as to form a bundle 500, for ease of discussion, bundle 500 and energy harvesting mechanism 500 will be used interchangeably; however, it will be appreciated that embodiments of energy harvesting mechanism 500 are not limited to the exact configurations shown or described for bundle 500 (e.g., in various embodiments, fibers 210 may not necessarily be bundled). When the cross-section of the central conductive rod 410 is about the same size as the cross-section of the PZT fiber 210, an embodiment provides that six PZT fibers 210 may surround the conductive rod 410 symmetrically, such as in the manner shown. However, non-symmetrical distributions are also contemplated. For example, in various alternative embodiments, non symmetrical distributions of fibers 210 can be utilized where owing to the placement of the fiber bundle 500 in the body, the deformation of the fiber bundle occurs preferentially in only a limited number of directions (e.g., only in one direction). This allows fibers 210 to be concentrated in a location around rod 410 in way such that they will be maximally deformed by deformation of bundle 500. In this way, the electrical signal (e.g., voltage, power etc) generated by deformation of the fibers 210 can be maximized for placement of the fiber bundle at a particular location in the body.

According to one or more embodiments, deformation of bundle 500 results in a particular direction results in certain PZT fibers 210 being maximally deformed while others may have minimal or no deformation. By having a number of PZT fibers distributed around core conductive rod 410, no matter what the direction of deformation of bundle 500, certain fibers 210 will always be deformed and thus always generate an electric voltage from that deformation due to their piezo electric properties (which convert mechanical deformation into electrical energy). A sufficient number of fibers 210 are desirably distributed around conductive rod 410 so that at least one or more fibers will always be deformed when bundle 500 is deformed no matter what the direction of deformation. In a preferred embodiment, at least six fibers are distributed around conductive rod 410, preferably in a symmetric fashion. In specific embodiments, 6, 8, 10, 12 or more fibers may be distributed around conductive rod 410. Still other numbers are contemplated. The number, distribution and material properties of PZT or other fibers 210 can be selected based upon the particular energy harvesting application including the location that bundle 500 is placed in or on the body. In particular, the stiffness of the fibers can be matched to the force, displacement and frequency of the particular bio-kinetic event. For example, in the case of various cardiac applications, the stiffness of the fibers can be selected so as to be deformed by the motion of the heart wall without interfering with that motion. Increased numbers of fibers 210 may be used to increase the likelihood of anyone fiber being deformed from deformation of the whole bundle 500.

In operation, adjacent peripheral conductive elements of 202 of each fiber 210 can form capacitive elements that are 'charged' when the region of the fiber 210 between the two adjacent elements is charged (e.g., due to deformation of that section of the fiber). The collection of peripheral conductive elements 202 on the fiber 210 provide a voltage source from which a power signal can be conducted through the central conductive element 410. In various embodiments, depending upon the amount and frequency of deformation, fiber bundle 500 can be configured to generate voltages in the range of about 1 to about 4 volts (with specific embodiments of 1, 1.2, 1.5 1.8, 2.5, 3.0. 3.3 and 3.6) and power in the range of 1 to 500 µwatts with a more preferred range of about 110 to 200 µwatts. Greater and lesser amounts are also contemplated. Production of desired voltages and powers can be achieved through selection of the material properties of the PZT fibers 210 (e.g., permittivity) as well as their number, length and diameter. In particular embodiments, the particular characteristics of the fiber bundle 500 (e.g., the total number of PZT fibers and their length and diameter) can be selected based upon the particular location that fiber bundle 500 is placed in the body (e.g., the heart), the biokinetic event used for energy harvesting purposes (e.g., the heartbeat) and the device to be powered (e.g., a pacemaker).

Figure 5C:
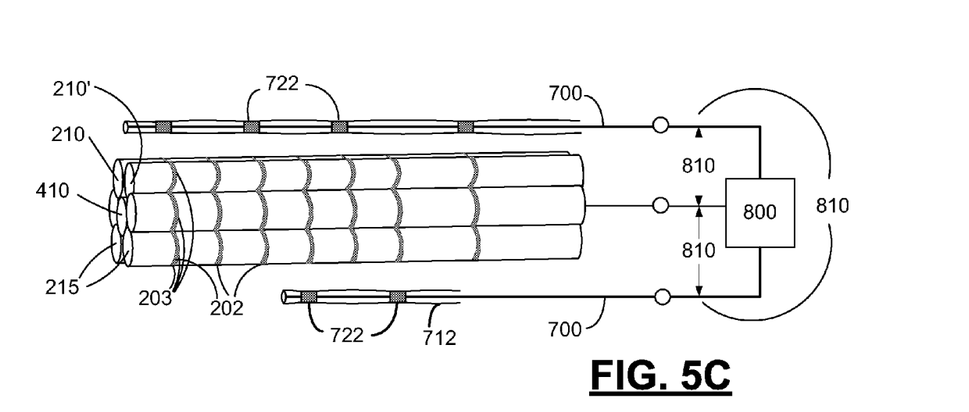
FIG. 5c is a perspective view of an embodiment of the energy harvesting mechanism/fiber bundle showing alignment of peripheral conductive elements of adjacent PCT fibers as well as the use of external conductive wire or other conductive member.
Figure 5D:
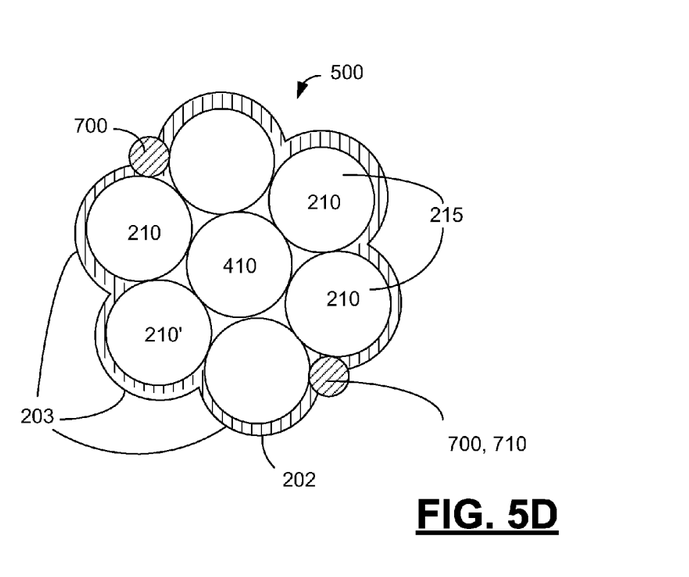
FIG. 5d is a cross sectional end view of the embodiment of FIG. 5c.
Figure 5E:
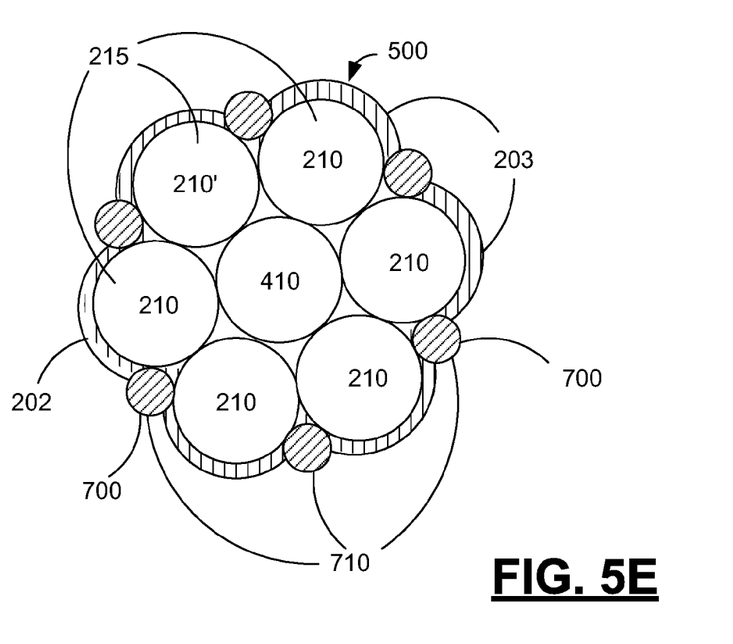
FIG. 5e is a cross sectional end view illustrating an embodiment of the mechanism/fiber bundle having a symmetrical distribution of external conductive members.

Referring now to FIGS. 5C-5E, in various embodiments, groups of peripheral conductive elements 202 of multiple PZT fibers 210 (which comprise a fiber group 215) can be aligned in parallel, so as to form a conductive element group 203. More specifically, a particular element 203 of a particular fiber 210 can be aligned with spatially corresponding elements 203 of other fibers 210 in group 215. As is shown in FIG. 5C, multiple groups 203 of peripheral conductive elements 202 can be so aligned. In use, embodiments having aligned elements groups 203 allow for the formation of a parallel circuit comprising current from all of the fibers in fiber group 215. This in turn, allows for the generation of an increased overall current due to the additive currents from deformation of multiple fibers 210 in fiber group 215. Also the use of grouped elements 203 allows for a single element 202 of the group to conduct all of the current resulting from the deformation of all of the fibers in group 215 and/or all of the fibers 210 making up bundle 500. Similarly, the use of grouped elements 203 also allows for the net electrical charge on element group 203 resulting from deformation of any of the PZT fibers in group 215 to be the sum of the net charges of the individual elements 202 in the group 203.

FIGS. 5C-5E also illustrate that in various embodiments fiber bundle 500 can include one or more external conductive wires or other conductive members 700. Similar to central rod 410, wires 700 will typically includes an insulative sheath or layer 712 that is patterned or otherwise formed on the periphery of the wire 700 so as to provide exposed conductive regions 722. Exposed regions 722 can then be aligned or otherwise matched up with conductive portions 202 so that current can flow between regions 722 and conductive portions 202.

Wires 700 provide an electrical or current path 810 for conducting current to electrical circuitry or components (e.g., a battery, capacitor, or other electrical storage device) of a device 800 that is powered by bundle 500. In some embodiments, only one wire 700 need be used. In these embodiments, the current path 810 to and from device 800 is formed using wire 700 and core conducting rod 410. In the embodiment shown in FIGS. 5C and 5D, bundle 500 includes two external conductive wires 700 such that the current path 810 is formed using both wires 700. In embodiments having two or more external wires 700, switching circuitry can be used to switch between use of core conductor 410 and external wires 700 as current path 810. Switching can be performed responsive to one or more electrical parameters (e.g., current, voltage, impedance) of the components of bundle 500 and/or device 800 so as to optimize the delivery of current and power to device 800. For example, should the impedance of a particular wire 700 exceed a threshold, switching circuitry can switch to the use of internal conductive rod 410 or another wire 700.

In some embodiments, bundle 500 may include only two external conductive wires 700 for purposes of forming current path 810 as is shown in the embodiment of FIGS. 5C and 5D. However in other embodiments, it may desirable to have a symmetrically distributed group 710 of wires 700 around fibers 210 as is shown in the embodiment of FIG. 5E. Such symmetrical configurations for wires 700 provide for more even bending and deformation of bundle 500 and thus fibers 210 by having a more symmetrical cross section for the entire fiber bundle. In these and related embodiments, switching circuitry can be used to select use of particular wires 700 for current path 810 out of the wire group 710. Alternatively, only one or two wires 700 of wire group 710 need have exposed conductive regions 722, while the remainder are completely covered by sheath 712 so as to be non-conductive.

Figure 6A:
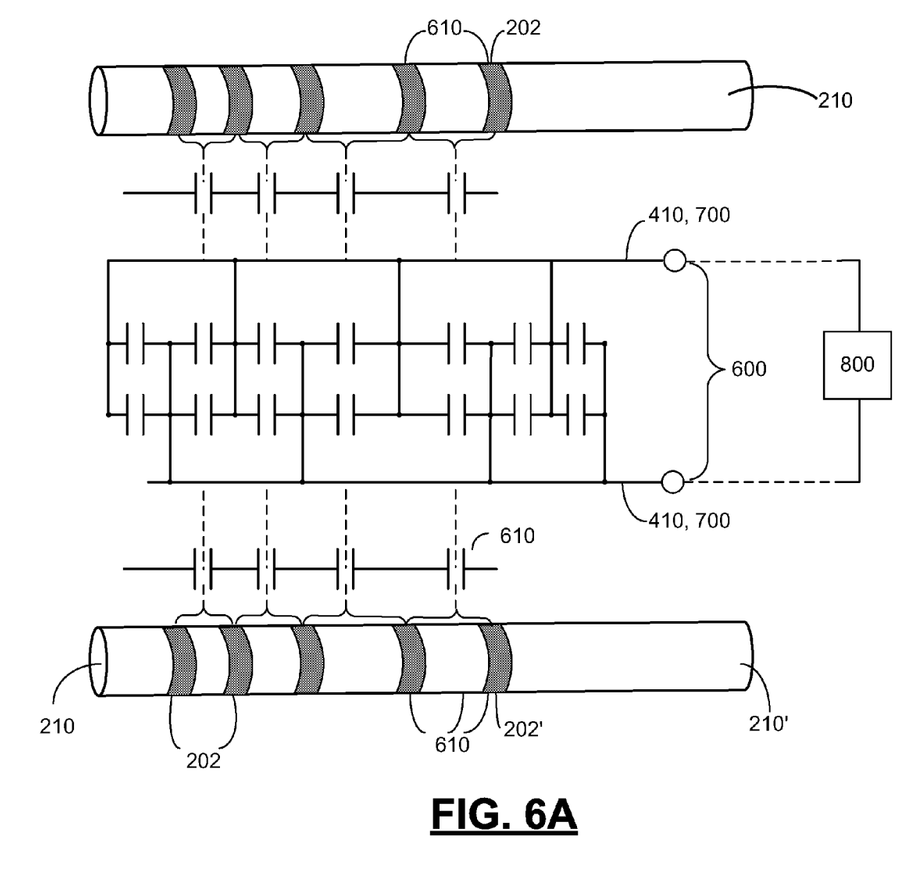
FIG. 6a is a schematic view illustrating how PZT portions of an embodiment of the energy harvesting mechanism can correspond to capacitive elements.
Figure 6B:
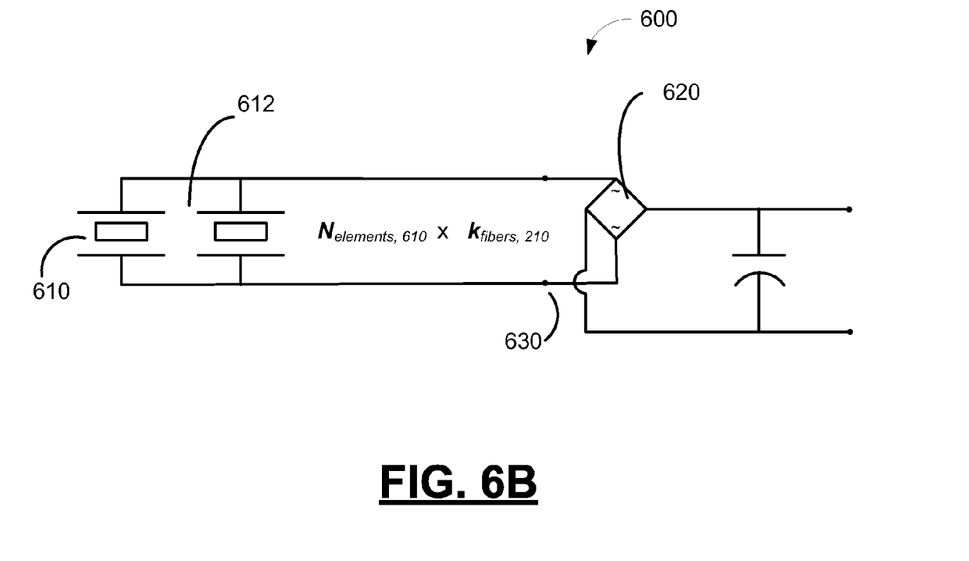
FIG. 6b is a schematic view illustrating an embodiment of a power supply circuit using an embodiment of the energy harvesting mechanism of the present invention.

Referring now to FIGS. 6A and 6B, these figures are representative diagrams that illustrate how the PZT fibers 210 and the axial conductive rod 410 and/or wire 700 combine to form a power supply circuit 600 for a biomedical or other device (or for a rechargeable battery or capacitor of such a device). FIG. 6A illustrates that each conductive element 202 of fibers 210 corresponds to a capacitive element 610.

The peripheral conductive elements 202 of each PZT fiber 210 may be considered to be aligned in parallel. Each fiber 210 may be aligned in parallel with an adjacent fiber 210' such that peripheral conductive elements 202 of one fiber align and make electrical contact with the peripheral conductive elements 202' of the adjacent fiber 210'. FIG. 6B shows a power supply circuit 600 that includes the capacitive elements 610 (n) of individual fibers (k) combining to provide a voltage source 630. A bridge rectifier 620 may be positioned on the circuit to rectify the voltage output 612 (n×k) of the individual fibers 610. In this way, AC type signals (e.g., voltages) resulting from pulsed bio-kinetic activities, such as a heart beat or arterial pulse, may be converted to a DC type signal for use in powering other devices in the host or those positioned at a different location from the mechanism.

According to an embodiment, the peripheral conductive elements 202 of the PZT fibers 210 may be aligned to connect to the exposed conductive regions 412 of the conductive rod 410 (FIG. 4A). A conductive epoxy, such as metal or other conductive epoxy, may be used to maintain the respective connections. Other conductive adhesives known in the art are also contemplated. Desirably, the conductive adhesive is selected and applied such that bundle 500 can bend, flex or otherwise deform in any direction while still maintaining the conductive contact between rod 410 and fibers 210. Still other conductive joining methods are also contemplated, such as the use of one or more conductive solders, solvent bonding, or hot melt junction methods known in the art (e.g. the use of a heated collete).

In various medical applications, bundles 500 may incorporated into the electrical leads of various implanted cardiac devices such as implantable pacemakers, where the leads are positioned in or adjacent the heart such that they bend and flex or otherwise deform from the motion of the beating heart and thus generate an electrical signal. The electrical signal can be used to power the cardiac device and/or as a sensor input to the device (e.g., an input corresponding to a pulse rate and/or a state of fibrillation). In other applications, bundles 500 can be positioned in the scaffolding/support structure of a vascular stent such that deformation of the stent (e.g. from radial expansion from an arterial pressure pulse) causes deformation of the fiber bundles and generation of an electrical signal. The electrical signal can be used to power a medical device coupled to bundle/mechanism 500 or as sensory input to an internal or external monitoring device (e.g. as an input corresponding to a blood pressure, pulse rate or like physiological parameter). Incorporation of bundle 500 into other stents and prosthetic structures such as various intestinal stents is also contemplated where expansion of the stent from a biokinetic event such as a peristaltic wave is used to generate an electrical signal.

In alternative applications, bundles 500 can be incorporated into the structure of various wind energy collectors such as sails or windmill blades such that deformation of the wind collector causes deformation of the bundle. In related embodiments they be adapted to be incorporated into existing pennants, flags, sails, windvanes and like objects and devices so that any of these can be converted into a portable wind energy collection system. In such embodiments, bundles 500 can comprise a strut or other structure that is inserted into the body or edge of the sail or pennant and deforms in response to the wind generated movement/deformation of the sail, pennant, flag or other materials that "flap" or kinetically receive wind.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. Embodiments of the harvesting mechanism can be adapted for any number of applications including powering various implanted pacemakers, defibrillators and other cardiac devices, spinal and nerve stimulators as well as insulin and other implanted drug pumps. They can also be adopted for use in harvesting energy from various wind energy applications described herein.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:
1. An energy harvesting mechanism comprising:
a central conductive element;
a plurality piezoelectric (PZT) fibers, each PZT fiber being positioned to be in contact with a corresponding peripheral length segment of the central conductive element, each PZT fiber deformable in a characteristic radial direction to convert its deformation into a corresponding electrical signal, each PZT fiber including a plurality of peripheral conductive elements provided on a periphery of the fiber, each conductive element including an insulative layer that is layered on a periphery of the conductive element to partially expose regions of the conductive element, wherein each PZT fiber is positioned relative to the central conductive element so that individual peripheral conductive ele- ments of the PZT fiber align with a corresponding exposed region of the conductive element; and wherein the plurality of PZT fibers are arranged so that any one of the plurality of PZT fibers is capable of being deformed in the characteristic radial direction to trigger the corresponding electrical signal.

2. The energy harvesting mechanism of claim 1, wherein each peripheral conductive element of each PZT fiber is aligned in a substantially parallel fashion with spatially corresponding peripheral conductive elements of other PZT fibers in the plurality to form a group of peripheral conductive elements so that the net charge on the group of peripheral conductive elements resulting from deformation of any of the PZT fibers in the plurality is the sum of the net charges of the individual peripheral conductive elements in the group.

3. The energy harvesting mechanism of claim 1, wherein the PZT fibers include aligned ferroelectric domains.

4. The energy harvesting mechanism of claim 1, wherein the PZT fibers comprise a ceramic or crystalline material.

5. The energy harvesting mechanism of claim 1, wherein the PZT fibers have a diameter in a range of about 20 to about 500 µm.

6. The energy harvesting mechanism of claim 5, wherein the PZT fibers have a diameter of about 100 µm.

7. The energy harvesting mechanism of claim 1, wherein two adjacent peripheral conductive elements on the same PZT fiber function as a capacitive element that is charged when a region of a PZT fiber bounded by those elements is charged.

8. The energy harvesting mechanism of claim 1, wherein a diameter of the central conductive element is equal or greater than a diameter of the PZT fibers.

9. The energy harvesting mechanism of claim 1, wherein the electrical signal comprises an electrical power signal.

10. The energy harvesting mechanism of claim 9, wherein the electrical power signal is in a range of about 1 to about 500 µwatts or about 110 to about 200 µwatts.

11. The energy harvesting mechanism of claim 1, wherein the PZT fibers are affixed to the central conductive element.

12. The energy harvesting mechanism of claim 1, wherein the PZT fibers are distributed around the central conductive element such that deformation of the plurality of PZT fibers in any direction will generate the electrical signal.

13. The energy harvesting mechanism of claim 1, wherein the PZT fibers have a substantially symmetric distribution around the central conductive element.

14. The energy harvesting mechanism of claim 1, wherein six PZT fibers are substantially symmetrically distributed around the central conductive element.

15. The energy harvesting mechanism of claim 1, wherein the central conductive element has a substantially cylindrical shape.

16. The energy harvesting mechanism of claim 1, wherein each PZT fiber has a substantially cylindrical shape.

17. The energy harvesting mechanism of claim 1, wherein the energy harvesting mechanism is configured to be incorporated into an electrical lead of a cardiac device and is configured to convert deformation of the lead caused by a beating heart into the electrical signal.

18. The energy harvesting mechanism of claim 17, wherein the cardiac device is an implanted pacemaker or defibrillator.

19. The energy harvesting mechanism of claim 1, wherein the energy harvesting mechanism is configured to be incorporated into an arterial scaffolding structure and is configured to convert deformation of the structure from an arterial pulse into an electrical signal.

20. An energy harvesting mechanism comprising:
a central conductive element;
a plurality piezoelectric (PZT) fibers, each PZT fiber being positioned to be in contact with a corresponding peripheral length segment of the central conductive element, each PZT fiber deformable in a characteristic radial direction to convert its deformation into a corresponding electrical signal, each PZT fiber including a plurality of peripheral conductive elements provided on a periphery of the fiber, each conductive element including an insulative layer that is layered on a periphery of the conductive element to partially expose regions of the conductive element, wherein each PZT fiber is positioned relative to the central conductive element so that individual peripheral conductive elements of the PZT fiber align with a corresponding exposed region of the conductive element, wherein the plurality of PZT fibers are arranged so that any one of the plurality of PZT fibers is capable of being deformed in the characteristic radial direction to trigger the corresponding electrical signal; and
wherein each peripheral conductive element of each PZT fiber is aligned in a substantially parallel fashion with spatially corresponding peripheral conductive elements of other PZT fibers in the plurality to form a group of peripheral conductive elements so that the electrical signal developed from deformation of any of the PZT fibers in the plurality of PZT fibers can be conducted through any of the peripheral conductive elements of the group.

* * * * *